United States Patent [19]

Cattoz et al.

[11] Patent Number: 5,117,030
[45] Date of Patent: May 26, 1992

[54] CATALYST/PROMOTER FOR DIRECT SYNTHESIS OF DIMETHYLDICHLOROSILANE

[75] Inventors: Roland Cattoz, Grigny; Guy Godde, Saint-Symphorien-D'Ozon; Jean-Louis Plagne, Lyons, all of France

[73] Assignee: Rhone-Poulenc Chimie, Courbevoie, France

[21] Appl. No.: 738,540

[22] Filed: Jul. 31, 1991

[30] Foreign Application Priority Data

Jul. 31, 1990 [FR] France .................... 90 10011

[51] Int. Cl.$^5$ ............................. C07F 7/16
[52] U.S. Cl. ...................... 556/472; 502/224; 502/225; 502/226; 502/227; 502/302; 502/303; 502/304; 502/343; 502/345; 502/353
[58] Field of Search ............... 556/472; 502/224, 226, 502/227, 225, 302, 303, 304, 343, 345, 353

[56] References Cited

U.S. PATENT DOCUMENTS 4,656,301  4/1987  Prud'Homme et al. ............ 556/472
4,661,613  4/1987  Prud'Homme et al. ............ 556/472

FOREIGN PATENT DOCUMENTS 0138679  4/1985  European Pat. Off. ............ 556/472
0138678  4/1985  France .
0194214  9/1986  France .

OTHER PUBLICATIONS

Chemical Abstracts, vol. 112, No. 15, Apr. 9, 1990, p. 667.
Chemical Abstracts, vol. 110, No. 6, 6 fevrier 1989, p. 146.

*Primary Examiner*—Paul F. Shaver
*Attorney, Agent, or Firm*—Burns, Doane, Swecker & Mathis

[57] ABSTRACT

Dimethyldichlorosilane is selectively and directly synthesized by reacting methyl chloride with silicon in the presence of ($\alpha$) a catalytically effective amount of metallic copper or a copper compound and a promoter ($\beta$) therefor, such promoter ($\beta$) comprising ($\beta_1$) metallic tin and/or metallic antimony or a tin and/or antimony compound, optionally, ($\beta_2$) metallic zinc or a zinc compound, and ($\beta_3$) at least one lanthanide compound; alternatively, the promoter ($\beta$) comprises ($\beta_1$), optionally, ($\beta_2$), ($\beta_3$) and ($\beta_4$) at least one alkali metal or alkali metal compound.

23 Claims, No Drawings

CATALYST/PROMOTER FOR DIRECT SYNTHESIS OF DIMETHYLDICHLOROSILANE

BACKGROUND OF THE INVENTION

1. Field of the Invention

The present invention relates to a novel process/catalyst for the direct synthesis of dimethyldichlorosilane.

2. Description of the Prior Art

The industrial process for the manufacture of organochlorosilanes and in particular of dimethyldichlorosilane, hereinafter designated DMCS, is well known to this art and is particularly described in U.S. Pat. No. 2,380,995, as well as in the text by Walter Noll, *Chemistry and Technology of Silicones*, pages 26–41, published by Academic Press Inc. (1968).

According to this so-called "direct synthesis" or "Rochow synthesis", organochlorosilanes, and in particular DMCS, are directly produced by reacting methyl chloride with a solid contact mass of silicon and of a catalyst containing copper, according to the reaction:

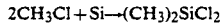

$$2CH_3Cl + Si \rightarrow (CH_3)_2SiCl_2$$

In actual fact, other products, especially methyltrichlorosilane $CH_3SiCl_3$, hereinafter designated MTCS, and trimethylchlorosilane $(CH_3)_3SiCl$, hereinafter designated TMCS, are formed during the direct synthesis. Other by-products are also formed, such as, for example, $(CH_3)HSiCl_2$ and $(CH_3)_2HSiCl$ and heavy products which are polysilanes, essentially disilanes.

Among all of such products produced by direct synthesis, DMCS is the most desired compound. After hydrolysis and polymerization, this compound enables the preparation of oils and resins which are basic starting materials for the production of silicones. Thus, DMCS is used for the preparation of polyorganosiloxane resins, as described in U.S. Pat. Nos. 2,258,218 to 2,258,222, for the preparation of oils as described in U.S. Pat. Nos. 2,469,888 and 2,469,830 and for the preparation of polyorganosiloxane elastomers as described in U.S. Pat. No. 2,448,756.

It is also known to this art to employ copper or compounds of copper as a catalyst for the above direct synthesis reaction, employed in the form of an alloy or mechanical admixture with silicon, optionally deposited onto an inorganic support.

To improve the DMCS yield, it too has been proposed to this art to add to the copper a promoter system containing one or more additives. These additives include zinc or a zinc halide (U.S. Pat. No. 2,464,033), aluminum (U.S. Pat. Nos. 2,403,370 and 2,427,605), tin, manganese, nickel and silver (British Pat. No. 1,207,466), cobalt (British Patent No. 907,161), potassium chloride (Russian Patent No. 307, 650), phosphorus or a phosphorus compound (U.S. Pat. No. 4,602,101), or arsenic or an arsenic compound (U.S. Pat. No. 4,762,940).

Such promoter systems based on the aforementioned additives undoubtedly improve the direct synthesis process, but they nevertheless present at least one of the following disadvantages:

(1) The selectivity for DMCS, evaluated as the average weight ratio MTCS/DMCS and/or as the molar % of DMCS relative to the total amount of the silanes produced, remains insufficient;

(2) The induction time and the initiation temperature of the reaction are too high;

(3) The mean activity of the catalyst system, also referred to as production efficiency, evaluated as the weight of methylchlorosilanes (MCS) produced per hour and per kg of silicon introduced, and the maximum degree of conversion o silicon remain insufficient;

(4) The catalyst system is sensitive to impurities; and (5) The formation of by-products and, in particular, of disilanes remains high.

European patents EP-A-0,138,678 and EP-A-0,138,679 describe the use of a copper catalyst comprising an improved promoter system which contains:

(i) 30 to 1000 ppm (calculated as the weight of metal relative to the weight of silicon employed) of at least one metal selected from tin and antimony or of a compound based on tin and/or antimony, (ii) 0.05% to 2% (calculated as indicated above) of at least one alkali metal selected from among lithium, sodium, potassium, rubidium and cesium or of a compound based on the same alkali metals, and (iii) optionally, 0.1% to 3% (calculated as indicated above) of metallic zinc or of a zinc-based compound.

When compared with a promoter system not comprising any alkali metal, the promoter systems described in the aforesaid European patents enable, when the reactions are used in one case and in the other case at appropriate temperatures and for similar periods of time resulting in equivalent consumptions of the Si introduced, attaining at least an appreciable increase in the selectivity for DMCS, evaluated, on the one hand, as the average weight ratio MTCS/DMCS and, on the other, as the molar % of DMCS relative to the total amount of silanes produced.

However, despite the advantages presented by the prior art catalysts and, in particular, those described in the aforesaid European patents, serious need continues to exist in this prior art for even further improved and/or more versatile catalyst systems which, depending on the particular reaction conditions selected to carry out the above direct synthesis on a industrial scale, permit determining with greater certainty the compound which is best suited to a given need.

SUMMARY OF THE INVENTION

Accordingly, one major object of the present invention is the provision of an improved process/catalyst for the direct synthesis of DMCS that does not require a promoter system containing any alkali metal, as do those described in the aforesaid European patents, but which nonetheless provide a selectivity for DMCS which is at least similar or slightly higher than that obtained using the known catalysts containing no alkali metal in their promoter system.

A second major object of the present invention is the provision of an alternative improved process/catalyst which, after one or more known additives comprising an alkali metal of the type of those described in said European patents has (have) been added thereto, provide at least one of the following advantageous results:

(1) A selectivity for DMCS which, on the one hand is always much higher than that attained using the prior art catalysts containing no alkali metal in their promoter system and, on the other, can even be higher than that attained using the improved catalysts according to the aforesaid European patents, indeed containing an alkali metal in their promoter systems;

(2) A selectivity which can be maintained at a high level in the event of a reaction temperature which is less high; and (3) A weight content of heavy by-products which, on the one hand, is always lower than that obtained using the prior art catalysts based on a promoter system containing no alkali metal and, on the other, which can be even lower than that obtained using the improved catalysts based on a promoter system indeed containing an alkali metal.

DETAILED DESCRIPTION OF THE PREFERRED EMBODIMENTS OF THE INVENTION

More particularly according to the present invention, in a first preferred embodiment thereof, a process for the production of dimethyldichlorosilane is featured, comprising reacting methyl chloride with a solid contact mass which comprises silicon and a catalyst comprising ($\alpha$) metallic copper or a copper-based compound and ($\beta$) a promoter system comprising;

(i) 10 to 1000 ppm (calculated as weight of tin and/or antimony metal relative to the weight of the silicon introduced) of an additive $\beta_1$ which comprises at least one metal selected from tin and antimony or from at least one tin- and/or antimony-based compound, (ii) 0% to 3% by weight (calculated as zinc metal relative to the weight of the silicon introduced) of an optional additive $\beta_2$ which comprises metallic zinc or of a zinc-based compound, and further comprising (iii) 0.01% to 2% by weight (calculated as metallic lanthanide relative to the weight of the silicon introduced) of a complementary additive $\beta_3$ comprising at least one lanthanide-based compound.

The catalyst is advantageously employed in a weight concentration of 1% to 30%, preferably 5% to 12%, relative to the total weight of the contact mass (calculated from the actual weight of the constituents).

The catalyst may be incorporated in the silicon in the form of an alloy, or in the form of a mechanical admixture.

Other than copper, it is possible to employ, as the copper-based compound, especially a copper halide, a copper oxide, for example CuO and Cu$_2$O, as described in U.S. Pat. No. 2,464,033.

It is preferred to employ a copper halide and, in this respect, cupric chloride or cuprous chloride are particularly exemplary. According to the present invention, better results are attained, especially in respect of selectivity and the degree of conversion of the silicon, if the copper is introduced in the form of cuprous or cupric chloride.

The copper portion ($\alpha$) of the catalyst is advantageously present in a weight concentration ranging from 0.1% to 20% and, preferably, from 1% to 10% by weight (calculated as copper metal relative to the weight of silicon introduced).

The weight content of tin and/or antimony or of tin- and/or antimony-based compound (calculated as tin and/or antimony metal) advantageously ranges from 10 to 1000 ppm and, preferably, from 20 to 200 ppm, relative to the weight of silicon introduced.

There must be at least 10 ppm of tin and/or antimony present. Indeed, it has been demonstrated in accordance with the invention that the beneficial effects of the lanthanide-based compound are obtained only in the presence of tin and/or antimony. In addition, a weight content higher than about 1,000 ppm would have an adverse effect on the reaction and especially on the selectivity thereof. Tin, which is the preferred metal, may be added in the form of bronze or in the form of a tin-based compound, for example tin chloride.

Zinc, when selected, is advantageously present in a weight concentration ranging from 0.1% to 3% and, preferably, from 0.2% to 1% by weight (calculated as zinc metal relative to the weight of the silicon). Up to 90% by weight of the zinc and preferably up to 50% of the zinc may be replaced by another metal which catalyzes copper chlorination and/or which forms a eutectic or a low melting point phase with the copper salts. Aluminum, cadmium, manganese, nickel and silver are representative such other metals.

By the term "lanthanide" are intended the metals in the Periodic Table of elements which have atomic numbers ranging from 57 to 71, as well as yttrium, which has similar properties, although having an atomic number of 39.

By the expression "lanthanide-based compound" are intended:

(i) an organic or inorganic derivative of any one of the lanthanides: cerium, lanthanum, praseodymium, neodymium, promethium, samarium, europium, gadolinium, terbium, dysprosium, holmium, erbium, ytterbium, thulium, lutetium and yttrium (the expression "at least one lanthanide-based compound" connotes that it is possible to introduce, other than a single derivative, a mixture of organic derivatives or a mixture of inorganic derivatives or a mixture of organic or inorganic derivatives of any one of the above-mentioned lanthanides);

(ii) a mixture of organic and/or inorganic derivatives or more than one of such lanthanides (the expression "at least one lanthanide-based compound" connotes that it is possible to introduce, other than a single mixture, a combination of a number of mixtures of this type).

In general, because of the relative amounts of the compounds of the various lanthanides in the most common ores, especially in monazite and bastnaesite, when a derivative of a single lanthanide is used, the latter is preferably cerium, lanthanum, praseodymium and neodymium. Cerium and lanthanum are the most abundant of these metals and are very particularly suitable.

Mixtures of derivatives of a plurality of lanthanides can also be employed. Indeed, it may prove advantageous not to carry out the lengthy and costly separation of all of the lanthanides present in relatively small amounts in the ores which are commonly treated. The following mixtures typically can be used in such events:

(i) a mixture of derivatives of cerium and one or more of the other lanthanides;

(ii) a mixture of derivatives of lanthanum and of one or more other lanthanides selected from among praseodymium, neodymium, promethium, samarium, europium, gadolinium, terbium, dysprosium, holmium, erbium, ytterbium, thulium, lutetium and yttrium;

(iii) a mixture of derivatives of praseodymium and of one or more other lanthanides selected from among neodymium, promethium, samarium, europium, gadolinium, terbium, dysprosium, holmium, erbium, ytterbium, thulium, lutetium and yttrium;

(iv) a mixture of derivatives of neodymium and of one or more other lanthanides selected from among promethium, samarium, europium, gadolinium, terbium, dysprosium, holmium, erbium, ytterbium, thulium, lutetium and yttrium.

When such mixtures of derivatives of a plurality of lanthanides are used in the process according to the invention, cerium and/or lanthanum and/or praseodymium and/or neodymium generally constitute at least 40 mol% of the total lanthanides.

It will be appreciated that the general definitions given above in respect of the lanthanides in connection with the expressions "compound based on" and "at least one compound based on" also apply to the same expressions which are given in connection with copper, tin, antimony or zinc-based compounds discussed above.

Particularly exemplary organic lanthanide derivatives include the salts in which the lanthanide cation is bonded to an organic anion of the following types: carboxylate emanating from an aliphatic and/or aromatic carboxylic acid having from 2 to 20 carbon atoms such as, for example, acetate, propionate, acrylate, methacrylate, glycolate, lactate and benzoate; organosulfonate emanating from an organosulfonic acid in which the organic moiety, which may be aliphatic and/or aromatic, has from 1 to 14 carbon atoms; and organophosphonate emanating from an organophosphonic acid in which the organic moiety, which may be aliphatic and/or aromatic, has from 1 to 14 carbon atoms.

Particularly exemplary inorganic lanthanide derivatives include the salts in which the lanthanide cation is bonded to an inorganic anion of the following types: nitrate, chloride, bromide, iodide, sulfate, sulfonate, perchlorate, phosphate, pyrophosphate, phosphite, selenate, vanadate or tungstate.

In the lanthanide derivatives employed in the process according to the invention, the lanthanide may be present in the various oxidation states exhibited thereby; in most cases, it is present in the oxidation state of III or IV.

In accordance with the above first preferred embodiment or first major object of the invention, the additive $\beta_3$ employed is the species $\beta_{3.1}$ comprising of at least one lanthanum (III), cerium (III) or cerium (IV) halide. More preferably, the additive $\beta_{3.2}$ comprises lanthanum (III) chloride and/or cerium (III) chloride.

The amount of lanthanide-based compound(s) used advantageously ranges from 0.01% to 2% by weight (calculated as metallic lanthanide relative to the weight of silicon introduced). Such amount preferably ranges from 0.03% to 1% by weight. Below 0.01%, the action of the lanthanide is not truly detectable and above 2% the lanthanide has a poisoning effect which lowers the reaction selectivity.

In a second preferred embodiment of the present invention, a process for the production of dimethyldichlorosilane is featured which comprises reacting methyl chloride with a solid contact mass comprising silicon and a catalyst which comprises ($\alpha$) metallic copper or a copper-based compound and ($\beta$) a promoter system comprising (i) 10 to 1000 ppm (calculated as weight of tin and/or antimony metal relative to the weight of silicon introduced) of an additive $\beta_1$ comprising at least one metal selected from tin and antimony or from at least one tin- and/or antimony-based compound, (ii) 0% to 3% by weight (calculated as zinc metal relative to the weight of silicon introduced) of an optional additive $\beta_2$ comprising metallic zinc or a zinc-based compound, (iii) 0.01% to 2% by weight (calculated as metallic lanthanide relative to the weight of silicon introduced) of a first complementary additive $\beta_3$ comprising at least on lanthanide-based compound, and (iv) 0.05% to 2% by weight (calculated as alkali metal relative to the weight of silicon introduced) of a second complementary additive $\beta_4$ comprising at least one alkali metal selected from among lithium, sodium, potassium, rubidium and cesium or at least one compound based on the same alkali metal or on a mixture of such alkali metals.

The above general and preferred definitions which relate to the copper fraction ($\alpha$) of the catalyst and to the additives $\beta_1$, $\beta_2$ and $\beta_3$ of the promoter system ($\beta$) are the same as those indicated above in connection with the description of the first preferred embodiment of the process of the invention. Other than pure metals, halides such as chlorides are employed as suitable additives $\beta_4$.

In a more preferred second embodiment of the invention, the promoter system ($\beta$) comprises the couple $\beta_{3.1}+\beta_{4.1}$, in which:

$\beta_{3.1}$ comprises at least one lanthanum (III), cerium (III) or cerium (IV) halide, and $\beta_{4.1}$ comprises at least one alkali metal selected from potassium and cesium or at least one halide derived from such metals.

In accordance with an even more preferred embodiment of the invention, the promoter system ($\beta$) comprises the couple $\beta_{3.2}+\beta_{4.2}$, in which:

$\beta_{3.2}$ comprises lanthanum (III) chloride and/or cerium (III) chloride, $\beta_{4.2}$ comprises cesium chloride.

In accordance with yet another more preferred embodiment of the invention, the promoter system ($\beta$) comprises the couple $\beta_{3.2}+\beta_{4.4}$, in which $\beta_{3.2}$ is as defined above and $\beta_{4.4}$ comprises a mixture of cesium and potassium chlorides.

Each additive of the promoter system ($\beta$) may be combined with the other additives or constituents of the contact mass by mechanical mixing which establishes an intimate contact among the constituents. It has been demonstrated, in accordance with the second embodiment of the present invention, that it is possible to provide a very appreciable increase, especially as regards the selectivity for DMCS, if the couples of additives $\beta_{3.1}+\beta_{4.1}$ in the form of halide, $\beta_{3.2}+\beta_{4.2}$, $\beta_{3.2}+\beta_{4.3}$ and $\beta_{3.2}+\beta_{4.4}$ are used directly in the form of a previously prepared mixed salt, hydrated or otherwise, which may be either a compound which has a perfectly defined chemical formula or a combination comprising a eutectic mixture or a mixture whose composition is close to or widely differing from a eutectic mixture.

In an especially preferred second embodiment of the invention, which presents the option of effectively and for the first time attaining a selectivity for DMCS as high as 0.030, mixed chlorides are employed, in either the anhydrous state or in hydrated form with one or more molecules of water, which are selected from among the following species: $Cs_3LaCl_6$, $Cs_3CeCl_6$, $KLa_2Cl_7$, $KLa_3Cl_{10}$, $K_2LaCl_5$, $K_3LACl_6$, $K_2CeCl_5$, $K_3Ce_2Cl_9$, $Cs_{1.5}K_{1.5}LaCl_6$ and mixtures of CsCl or of KCl with $LaCl_3$ or $CeCl_3$ containing 5% to 95% by weight of alkali metal chloride.

These mixed chlorides are known salts. A number of operating techniques which produce equivalent results are possible; it is possible, for example, to prepare these mixed salts by mixing the necessary amounts of lanthanide chloride and alkali metal chloride in solution (water or any other solvent). It is also possible to employ a melt route (cf., especially, G.N. Papatheodorgy, *Inorg. Nucl. Chem. Letters*, vol. 11, page 483 (1975)).

The amount of lanthanide-based compound(s) $\beta_3$ is that indicated above in connection with the first preferred embodiment of the invention. It thus ranges from 0.01% to 2% by weight and, preferably, from 0.03% to 1% by weight (calculated as metallic lanthanide relative to the weight of silicon).

As regards the weight content of the alkali metal or of alkali metal-based compound(s) $\beta_4$, this ranges from 0.05% to 2% by weight (calculated as alkali metal relative to the same reference). Amounts ranging from 0.1% to 1.5% by weight are preferably employed. Below 0.05% the action of the alkali metal is not truly detectable and above 2% by weight the alkali metal has a poisoning effect.

More preferably, the amounts of the lanthanide $\beta_3$ and alkali metal $\beta_4$ additives are selected within the aforementioned general and preferred ranges such that the ratio:

weight of alkali metal/weight of lanthanide metal ranges from 0.05% to 100% and preferably from 0.1% to 20%.

Furthermore, it is desirable that the particle size of the silicon should be such that the diameter of at least 50% by weight of the particles ranges from 10 to 500 μm.

Similarly, the catalyst is also in the form of particles whose mean diameter advantageously ranges from 1 to 100 μm. Under these conditions of particle size of the contact mass, the direct synthesis reaction can be carried out using a contact mass, in the form of a fluidized bed.

The direct synthesis according to the invention can generally be carried out in one of the following three types of apparatus: a reactor of the stirred bed type as described in U.S. Pat. No. 2,449,821, a reactor of the fluidized bed type as described in U.S. Pat. No. 2,389,931, or in a rotary oven.

The catalyst may also be employed deposited onto a particular inorganic substrate such as sand, ground silica, silica gel, alumina, ground refractory brick, petroleum cracking catalysts, zeolites and calcined clays, as described in FR-A-1,545,407.

The reaction is advantageously carried out at a temperature ranging from 280° and 450° C., preferably from 290° to 370° C.

The reaction may be carried out directly at the temperature selected without initiating the reaction at a higher temperature, in particular when the reaction temperature selected is on the order of 330° C.

If the reaction is carried out at a temperature below 330° C., it is desirable to initiate the reaction for a few tens of minutes to 1 hour, or longer, at a temperature above 330° C.

In order to further illustrate the present invention and the advantages thereof, the following specific examples are given, it being understood that same are intended only as illustrative and in nowise limitative.

Unless otherwise indicated, a cylindrical pilot reactor was used in said examples to follow that had an internal diameter of 60 mm and a height of 250 mm, fitted with a sintered glass gas distributor at its base. The silicon and the catalyst were charged therein in the form of a powder in which the mean size of at least 50% of the particles ranged from 60 to 200μm. The reaction was carried out in a stirred bed and the reactor was equipped with external heating means.

EXAMPLE 1

$CuCl/Sn/ZnCl_2/LaCl_3$ catalyst system at 315° C.

A powdered contact mass composed of the following materials was charged into a cylindrical vertical glass reactor (60 mm diameter), fitted with a metal stirrer and a sintered glass gas distributor:

(i) silicon: 210 g,
(ii) CuCl: 16.3 g (i.e., 5% of Cu metal relative to Si),
(iii) bronze containing 10% by weight of Sn: 0.38 g (i.e., 0.018% of Sn metal relative to Si),
(iv) $ZnCl_2$: 1.60 g (i.e., 0.37% of Zn metal relative to Si), and
(v) $LaCl_3.6H_2O$: 0.68 g (i.e., 0.13% of La metal relative to Si).

The reactor was heated progressively to 200° C. under a nitrogen stream. Then, while continuing to increase the reactor temperature, the nitrogen stopcock was closed and introduction of methyl chloride was initiated at a flow rate (measure at 20° C.) of 16 l/h.

After an induction stage at 345° C. for 1 hour, the reaction temperature was decreased to 315° C. for the remainder of the reaction.

The chlorosilanes produced were sampled and analyzed at regular intervals by vapor phase chromatography. The results reported below take account of all chlorosilanes which were produced between the degree of conversion of the silicon charged (DCSi) equal to zero and the degree of conversion indicated below. The chlorosilanes produced during the induction stage were therefore included in the results which follow.

In this example, as in the example which follow, for purposes of uniformity, all results are reported for DCSi situated in the range 55% to 60%, it should be understood, however, that the reaction may be continued beyond this and may attain a maximum value of DCSi as high as those ranging from 70% to 88%.

After 56% of the silicon introduced had been consumed (DCSi=56%), the following results were obtained:

| (a) | Production efficiency (g of MCS/h/kg of Si) | 129 |
|---|---|---|
| (b) | Composition in mol % relative to the total amount of silanes obtained, as: | |
| | $(CH_3)_2SiCl_2$ or DMCS | 87.6 |
| | $CH_3SiCl_3$ or MTCS | 5.2 |
| | $(CH_3)_3SiCl$ or TMCS | 2.8 |
| (c) | Selectivity: average weight ratio MTCS/DMCS | 0.069 |
| (d) | % by weight of heavy fraction obtained relative to methylchlorosilane (MCS) | 4.6 |

COMPARATIVE EXAMPLE 1

Catalyst system: $CuCl/Sn/ZnCl_2$ at 300° C.

The procedure of Example 1 was repeated, except that the contact mass included lanthanum (III) chloride.

The following results were obtained at a DCSi of 56%:

| (a) | Production efficiency | 140 |
|---|---|---|
| (b) | Composition: | |
| | DMCS | 87.2 |
| | MTCS | 5.7 |
| | TMCS | 2.9 |
| (c) | Selectivity | 0.076 |

-continued

| (d) | % Heavy fraction | 4.7 |

EXAMPLE 2

Catalyst system: $CuCl/Sn/ZnCl_2/Cs_3LaCl_6$ at 315° C.

The procedure of Example 1, was repeated, except that, in the contact mass, the 0.68 g of $LaCl_3.6H_2O$ was replaced with 1.58 g of mixed cesium lanthanum (III) chloride of formula $CsLaCl_6$ (i.e., 0.39% of Cs metal and 0.13% of La metal relative to Si; with a weight ratio: Cs metal/La metal = 3).

The mixed chloride $Cs_3LaCl_6$ had been prepared by providing an aqueous solution of the appropriate amounts of CsCl and of $LaCl_3$, followed by slow evaporation of the solvent at 65° C. at $30 \times 10^2$ Pa and by drying the resulting white solids in an oven at 120° C.

The following results were obtained at a DCSi of 59%:

| (a) | Production efficiency | 125 |
| (b) | Composition: | |
| | DMCS | 94.3 |
| | MTCS | 2.4 |
| | TMCS | 1.5 |
| (c) | Selectivity | 0.0303 |
| (d) | % Heavy fraction | 1.8 |

COMPARATIVE EXAMPLE 2

Catalyst system: $CuCl/Sn/ZnCl_2/CsCl$ at 315° C.

The procedure of Example 2, was repeated, except that, in the contact mass, the 1.58 g of $Cs_3LaCl_6$ was replaced with 1.063 g of CsCl (i.e., 0.39% of Cs metal relative to Si).

The following results were obtained at a DCSi of 59%:

| (a) | Production efficiency | 139 |
| (b) | Composition: | |
| | DMCS | 92.9 |
| | MTCS | 3.0 |
| | TMCS | 2.0 |
| (c) | Selectivity | 0.037 |
| (d) | % Heavy fraction | 2.4 |

EXAMPLE 3

Catalyst system: $CuCl/Sn/ZnCl_2/Cs_{1.5}K_{1.5}LaCl_6$ at 315° C.

The procedure of Example 2 was repeated, except that, in the contact mass, the 1.58 g of $Cs_3LaCl_6$ was replaced with 2.4 g of the mixed cesium potassium lanthanum (III) chloride of the formula $Cs_{1.5}K_{1.5}LaCl_6$ (i.e., 0.37% of Cs metal, 0.11% of K metal and 0.26% of La metal relative to Si; with a weight ratio: alkali metals/La metal = 1.85).

This mixed chloride had been prepared by the solution route according to the operating technique set forth in Example 2.

This following results were obtained for a DCSi of 57%:

| (a) | Production efficiency | 133 |
| (b) | Composition: | |

-continued

| | DMCS | 93.7 |
| | MTCS | 2.5 |
| | TMCS | 1.6 |
| (c) | Selectivity | 0.031 |
| (d) | % Heavy fraction | 2.5 |

EXAMPLE 4

Catalyst system: $CuCl/Sn/ZnCl_2/K_3LaCl_6$ at 315° C.

The procedure of Example 2 was repeated, except that, in the contact mass, the 1.58 g of $Cs_3LaCl_6$ was replaced with 1.69 g of the mixed potassium lanthanum (III) chloride of the formula $K_3LaCl_6$ (i.e., 0.2% of K metal, 0.24% of La metal relative to Si; with a weight ratio: k metal/La metal = 0.833).

The following results were obtained at a DCSi of 58%:

| (a) | Production | 121 |
| (b) | Composition: | |
| | DMCS | 93.6 |
| | MTCS | 2.8 |
| | TMCS | 1.7 |
| (c) | Selectivity | 0.035 |
| (d) | % Heavy fraction | 1.8 |

COMPARATIVE EXAMPLE 3

Catalyst system: $CuCl/Sn/ZnCl_2/KCl$ at 315° C.

The procedure of Example 4 was repeated, except that in the contact mass, the 1.69 g of mixed salt $K_3LaCl_6$ was replaced with 0.81 g of KCl (i.e., 0.2% of K metal relative to Si).

The following results were obtained at a DCSi of 59%.

| (a) | Production efficiency | 151 |
| (b) | Composition: | |
| | DMCS | 90.6 |
| | MTCS | 3.8 |
| | TMCS | 2.7 |
| (c) | Selectivity | 0.049 |
| (d) | % Heavy fraction | 3.5 |

EXAMPLES 5 and 6

The procedure of Example 2 was repeated, except that the composition of the contact mass (Examples 5 and 6) and the temperature (Example 6) were modified.

With respect to the contact mass, the composition employed in Example 2 was used, which was modified by replacing the 1.58 g of $Cs_3LaCl_6$ with 1.22 g of a eutectic mixture of cesium chloride and lanthanum (III) chloride containing 87.7% by weight of CsCl and 12.3% by weight of $LaCl_3$ (i.e., 0.4% of Cs metal and 0.04% of La metal relative to Si; with a weight ratio: Cs metal/La metal = 10).

The results obtained are reported in the following Table:

TABLE

| EXAMPLE | 5 | 6 |
|---|---|---|
| Temperature (°C.) initiation | 345 | 345 |
| reaction | 315 | 300 |
| DCSi (%) | 58 | 58 |
| Production efficiency | 154 | 134 |

TABLE-continued

| EXAMPLE | 5 | 6 |
|---|---|---|
| Composition: | | |
| DMCS | 92.6 | 92.7 |
| MTCS | 2.9 | 2.7 |
| TMCS | 1.9 | 1.9 |
| Selectivity | 0.036 | 0.034 |
| % Heavy fraction | 3.0 | 3.4 |

EXAMPLE 7

Catalyst system: $CuCl/Sn/ZnCl_2/Cs_3CiCl_6$ at 315° C.

The procedure of Example 2 was repeated, except that, in the contact mass, the 1.58 g of $Cs_3LaCl_6$ was replaced with 1.58 g of mixed cesium cerium (III) chloride of the formula $Cs_3CeCl_6$ (i.e. 0.4% of Cs metal and 0.14% of Ce metal relative to Si; with a weight ratio: Cs metal/Ce metal=2.85).

The mixed chloride had been prepared by the solution route according to the operating technique set forth in Example 2 by carrying out the evaporation at a temperature of approximately 40° C.

The following results were obtained at a DCSi of 57%:

| (a) | Production efficiency | 148 |
|---|---|---|
| (b) | Composition: | |
| | DMCS | 91.6 |
| | MTCS | 3.0 |
| | TMCS | 2.1 |
| (c) | Selectivity | 0.038 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the direct synthesis of dimethyldichlorosilane, which comprises reacting methyl chloride with silicon in the presence of ($\alpha$) a catalytically effective amount of metallic copper or a copper compound and a promoter ($\beta$) therefor, said promoter ($\beta$) comprising ($\beta_1$) metallic tin and/or metallic antimony or a tin and/or antimony compound and ($\beta_3$) at least one lanthanide compound.

2. The process as defined by claim 1, said promoter ($\beta$) further comprising ($\beta_4$) at least one alkali metal or alkali metal compound.

3. The process as defined by claims 1 or 2, said promoter ($\beta$) further comprising ($\beta_2$) metallic zinc or a zinc compound.

4. The process as defined by claim 2, said at least one alkali metal or alkali metal compound comprising lithium, sodium, potassium, rubidium or cesium.

5. The process as defined by claim 1, said promoter ($\beta$) comprising from 10 to 1000 ppm of ($\beta_1$) and 0.01% to 2% by weight of ($\beta_3$).

6. The process as defined by claim 2, said promoter ($\beta$) comprising from 10 to 1000 ppm of ($\beta_1$), 0.01% to 2% by weight of ($\beta_3$) and 0.05% to 2% by weight of ($\beta_4$).

7. The process as defined by claims 5 or 6, said promoter ($\beta$) comprising from 20 to 200 ppm of ($\beta_1$).

8. The process as defined by claim 3, said promoter ($\beta$) comprising up to 3% by weight of ($\beta_2$).

9. The process as defined by claim 8, said promoter ($\beta$) comprising from 0.2% to 1% by weight of ($\beta_2$).

10. The process as defined by claims 1 or 2, said catalyst ($\alpha$) comprising cuprous chloride or cupric chloride.

11. The process as defined by claims 1 or 2, said promoter ($\beta$) comprising ($\beta_3$) a lanthanum (III), cerium (III) or cerium (IV) halide.

12. The process as defined by claim 11, said promoter ($\beta$) comprising ($\beta_3$) lanthanum (III) chloride and/or cerium (III) chloride.

13. The process as defined by claim 2, said promoter ($\beta$) comprising ($\beta_3$) at least one lanthanum (III), cerium (III) or cerium (IV) halide and ($\beta_4$) at least one of potassium and/or cesium or at least one halide thereof.

14. The process as defined by claim 2, said promoter ($\beta$) comprising ($\beta_3$) lanthanum (III) chloride and/or cerium (III) chloride and ($\beta_4$) cesium chloride.

15. The process as defined by claim 2, said promoter ($\beta$) comprising ($\beta_3$) lanthanum (III) chloride and/or cerium (III) chloride and ($\beta_4$) potassium chloride.

16. The process as defined by claim 2, said promoter ($\beta$) comprising ($\beta_3$) lanthanum (III) chloride and/or cerium (III) chloride and ($\beta_4$) cesium chloride and potassium chloride.

17. The process as defined by any one of claims 13 to 16, wherein ($\beta_3$)+($\beta_4$) comprises a mixed salt or hydrate or eutectic composition thereof.

18. The process as defined by claim 17, wherein ($\beta_3$)+($\beta_4$) comprises $Cs_3LaCl_6$, $Cs_3CeCl_6$, $KLa_2Cl_7$, $KLa_3Cl_{10}$, $K_2LaCl_5$, $K_3LaCl_6$, $K_2CeCl_5$, $K_3Ce_2Cl_9$, $Cs_{1.5}K_{1.5}LaCl_6$ or admixture of CsCl or KCl with $LaCl_3$ or $CeCl_3$.

19. The process as defined by claim 2, wherein said promoter ($\beta$) the ratio by weight of the alkali metal to the lanthanide metal ranges from 0.05 to 100.

20. The process as defined by claim 19, said ratio ranging from 0.1 to 20.

21. A composition of matter comprising ($\alpha$) a catalytically effective amount of metallic copper or a copper compound and a promoter ($\beta$) therefor, said promoter ($\beta$) comprising ($\beta_1$) metallic tin and/or metallic antimony or a tin and/or antimony compound and ($\beta_3$) at least one lanthanide compound.

22. The composition of matter as defined by claim 21, said promoter ($\beta$) further comprising ($\beta_4$) at least one alkali metal or alkali metal compound.

23. The composition of matter as defined by claims 21 or 22, said promoter ($\beta$) further comprising ($\beta_2$) metallic zinc or a zinc compound.

* * * * *